United States Patent [19]

Brooks et al.

[11] Patent Number: 4,963,541
[45] Date of Patent: Oct. 16, 1990

[54] PYRIMIDO-PYRIMIDINE LIPOXYGENASE INHIBITING COMPOUNDS

[75] Inventors: Dee W. Brooks, Libertyville; Anwer Basha, Lake Forest, both of Ill.

[73] Assignee: Abbott Laboratories, Abbott Park, Ill.

[21] Appl. No.: 314,008

[22] Filed: Feb. 22, 1989

[51] Int. Cl.$^5$ .................. A61K 31/505; A61K 31/535
[52] U.S. Cl. ..................... 514/183; 514/212; 514/234.2; 514/234.5; 514/258
[58] Field of Search ....................... 544/256, 118, 122; 540/600, 481; 514/258, 234.5, 212, 183, 234.2; 435/184

[56] References Cited

U.S. PATENT DOCUMENTS

| | | | |
|---|---|---|---|
| 3,031,450 | 4/1962 | Fischer et al. | 540/600 |
| 4,393,075 | 7/1983 | Terao et al. | 424/304 |

FOREIGN PATENT DOCUMENTS

| | | | |
|---|---|---|---|
| 0678353 | 1/1964 | Canada | 514/258 |
| 0104468 | 4/1984 | European Pat. Off. | |
| 0121806 | 10/1984 | European Pat. Off. | |
| 0128374 | 12/1984 | European Pat. Off. | |
| 0169405 | 1/1986 | European Pat. Off. | 514/258 |
| 2300661 | 7/1974 | Fed. Rep. of Germany | |
| 0736917 | 7/1969 | France | 544/256 |
| 807826 | 1/1959 | United Kingdom | |

OTHER PUBLICATIONS

Corey et al., J. Am. Chem. Soc. 1984, 106, 1503–1504 "Rationally Designed Potent Competitive Inhibitors of Leukotriene Biosynthesis".
Radmark et al., FEBS Lett., 110, 213 (1980), "The Inhibitory Effects of BW 755C on Arachidonic Acid Metabolism in Human Polymorphonuclear Leukocytes".
Morris et al., Prostaglandins, 10, (1980), "The Role of Arachidonate Lipoxygenase in the Release of SRS-A from Guinea-pig Chopped Lung".
Coutts, Meeting Abstract 70, Prostaglandins and Leukotrienes, '84, "Arylmethyl Phenyl Esthers: A New Class of Specific Inhibitors of 5-Lipoxygenase".
Walker et al., Pharm. Pharmacol., 31, 778, (1979), "Inhibition of Rabbit PMN Lipoxygenase Activity by Benoxaprofen".
Carter et al., Federation Proceedings, 44(4):904, 1985, "Dipyrodamole: A Potent and Specific 5-Lipoxygenase Inhibitor".
Pichler et al., Drugs of the Future, 8, 1023, 1983, "RA-642".

Primary Examiner—Mukund J. Shah
Assistant Examiner—Edward C. Ward
Attorney, Agent, or Firm—Jerry F. Janssen; Steven F. Weinstock

[57] ABSTRACT

Compounds of the formula:

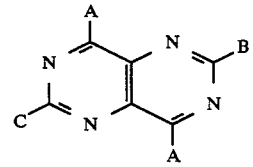

wherein A is selected from $NR_1R_2$ and $N(OR_6)R_2$; and B and C are chloro when A is $N(OR_6)R_2$ or are independently selected from $NHR_3$ and $NR_4R_5$ where $R_1$, $R_2$, $R_3$, $R_4$ and $R_5$ are independently selected from the group consisting of alkyl, cycloalkyl and alkylaryl each of which may be unsubstituted or substituted with one or more substituents selected from the group consisting of hydroxy, OR, NRR, OCOR, OCONRR, NRCOR and NRCONRR where R is selected from the group consisting of hydrogen, alkyl, aryl, alkylaryl, alkoxy and hydroxy or $R_1$ and $R_2$ or $R_4$ and $R_5$ together can form a heteroaryl group and $R_6$ is a member selected from the group consisting of hydrogen, alkyl, alkylaryl and trialkylsilyl; and the pharmaceutically acceptable salts thereof.

These compounds are useful as inhibitors of lipoxygenase enzymes.

3 Claims, No Drawings

PYRIMIDO-PYRIMIDINE LIPOXYGENASE INHIBITING COMPOUNDS

Technical Field

This invention relates to compounds which inhibit lipoxygenase enzymes. It also relates to methods of inhibiting lipoxygenase enzymes in human and animal hosts in need of such treatment.

The lipoxygenases are a family of enzymes which catalyze the oxygenation of arachidonic acid. The enzyme 5-lipoxygenase converts arachidonic acid to 5-hydroperoxyeicosatetraenoic acid (5-HPETE). This is the first step in the metabolic pathway yielding 5-hydroxyeicosatetraenoic acid (5-HETE) and the important class of mediators, the leukotrienes (LTs). Similarly 12- and 15-lipoxygenase, convert arachidonic acid to 12- and 15-HPETE respectively. Biochemical reduction of 12-HPETE leads to 12-HETE, while 15-HPETE is the precursor of the class of biological agents known as the lipoxins.

A variety of biological effects are associated with these products from lipoxygenase metabolism of arachidonic acid and they have been implicated as mediators in various disease states. For example, the LTs $C_4$ and $D_4$ are potent constrictors of human airways in vitro and aerosol administration of these substances to non-asthmatic volunteers induces broncho-constriction. $LTB_4$ and 5-HETE are potent chemotactic factors for inflammatory cells such as polymorphonuclear leukocytes. They also have been found in the synovial fluid of rheumatoid arthritic patients. The biological activity of the LTs has been reviewed by Lewis and Austin (J. Clinical Invest. 73, 889, 1984) and by Sirois (Adv. Lipid Res. 21, 78, 1985).

Thus, lipoxygenase enzymes play an important role in the biosynthesis of mediators of asthma, allergy, arthritis, psoriasis, and inflammation. Blocking these enzymes interrupts the biochemical pathways involved in these disease states.

Background Art

Relatively few compounds are known from the prior art which are inhibitors of the lipoxygenase enzymes. Among the lipoxygenase inhibitors known to the art are: AA-861, a 5-lipoxygenase inhibitor, disclosed in U.S. Pat. No. 4,393,075, issued July 12, 1983 to Terao et al.; pyrazolo pyridines, which are 5-lipoxygenase inhibitors, disclosed in European Patent Application of Irikura et al., S.N. 121,806, published Oct. 17, 1984; arachidonyl hydroxamic acid, a 5-lipoxygenase inhibitor, disclosed in E. J. Corey et al., *J. Am. Chem. Soc.*, 106, 1503 (1984) and European Patent Application of P. H. Nelson, S.N. 104,468, published April 4, 1984; BW755C, an inhibitor of 5- and 12-lipoxygenases, disclosed in Radmark et al., *FEBS Lett.*, 110, 213 (1980); nordihydro-guariaretic acid, an inhibitor of 5- and 15-lipoxygenases, disclosed in Morris et al., *Prostaglandins*, 19, (1980); REV-5901, a 5-lipoxygenase inhibitor, disclosed in Coutts, Meeting Abstract 70, *Prostaglandins and Leukotrienes* '84; quinoline N-oxides, 5-lipoxygenase inhibitors disclosed in European patent application of Hashizumo et al., S.N. 128,374, published Dec. 19, 1984 and benoxaprofen, disclosed in J. Walker, *Pharm. Pharmacol.*, 31, 778 (1979).

Some pyrimidopyrimidine compounds are known to be biologically active. For example, dipyridamole, 2,6-bis-(diethanolamino)-4,8-dipiperidinopyrimido[5,4-d]pyrimidine, is a coronary vasodilator (British Patent No. 807,826) and was reported to be an inhibitor of 5-lipoxygenase (P. R. Young, R. D. Dyer, G. W. Carter, Federation Proceedings 44(4):904, 1985). Similar compounds are reported in Japan Kokai 7759190, 7759191 (1977); 2,6-bis-(diethanolamino)-4-piperidinopyrimido[5,4d]pyridimine was shown to inhibit tumor cell growth in rats (Ger. Offen. 2931, 573); and 2,6-bis-(2-hydroxyethyl-2-methoxyethylamino)-4,8-bis-(diethylamino)pyrimido[5,4-d]pyrimidine is reported to be a hypertensive agent (Drugs of the Future, 8, 1023, 1983).

Summary of the Invention

The compounds of this invention possess unexpected activity as inhibitors of lipoxygenase enzymes, and reduce the biosynthesis of leukotrienes $B_4$, $C_4$, $D_4$ and $E_4$. The compounds and compositions containing these compounds are useful for the treatment of disease states, in mammals, which involve leukotrienes $B_4$, $C_4$, $D_4$ and $E_4$.

The novel compounds of this invention are those of Formula I:

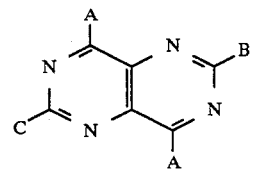

wherein A is selected from $NR_1R_2$ and $N(OR_6)R_2$; and B and C are chloro when A is $N(OR_6)R_2$ or are independently selected from $NHR_3$ and $NR_4R_5$ where $R_1$, $R_2$, $R_3$, $R_4$ and $R_5$ are independently selected from the group consisting of alkyl, cycloalkyl and alkylaryl each of which may be unsubstituted or substituted with one or more substituents selected from the group consisting of hydroxy, OR, NRR, OCOR, OCONRR, NRCOR and NRCONRR where R is selected from the group consisting of hydrogen, alkyl, aryl, alkylaryl, alkoxy and hydroxy or $R_1$ and $R_2$ or $R_4$ and $R_5$ together can form a heteroaryl group and $R_6$ is a member selected from the group consisting of hydrogen, alkyl, alkylaryl and trialkylsilyl; provided that A, B and C cannot be identical, A cannot be piperidino, ethanolamino, diethanolamino, ethylpropylamino, ethylbutylamino or $N(C_{12}H_{25})CH_2CH_2OH$, B and C cannot be diethanolamino or $N(CH_2CH_2OH)CH_2CH_2OCH_3$ and when A is $NR_1R_2$ and $R_1$ and $R_2$ are alkyl, they must be different; and the pharmaceutically acceptable salts thereof.

This invention also relates to pharmaceutical compositions and methods of inhibiting lipoxygenase enzymes and related disorders comprising the administration to a mammal, preferably a human, in need of such treatment of a compound of Formula II:

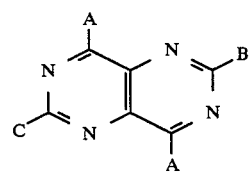

wherein A is selected from $NR_1R_2$ and $N(OR_6)R_2$; and B and C are chloro when A is $N(OR_6)R_2$ or are independently selected from $NHR_3$ and $NR_4R_5$ where $R_1$, $R_2$, $R_3$, $R_4$ and $R_5$ are independently selected from the group consisting of alkyl, cycloalkyl and alkylaryl each of which may be unsubstituted or substituted with one or more substituents selected from the group consisting of hydroxy, OR, NRR, OCOR, OCONRR, NRCOR and NRCONRR where R is selected from the group consisting of hydrogen, alkyl, aryl, alkylaryl, alkoxy and hydroxy or $R_1$ and $R_2$ or $R_4$ and $R_5$ together can form a heteroaryl group and $R_6$ is a member selected from the group consisting of hydrogen, alkyl, alkylaryl and trialkylsilyl; and the pharmaceutically acceptable salts thereof.

Detailed Description of Preferred Embodiments

The compounds of this invention possess unexpected activity as inhibitors of lipoxygenase enzymes, and reduce the biosynthesis of leukotrienes $B_4$, $C_4$, $D_4$ and $E_4$. The compounds and compositions containing these compounds are useful for the treatment of disease states, in mammals, which involve leukotrienes $B_4$, $C_4$, $D_4$ and $E_4$.

The compounds of this invention are those of Formula I:

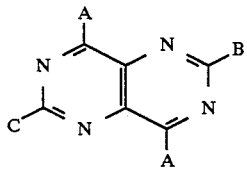

wherein A is selected from $NR_1R_2$ and $N(OR_6)R_2$; and B and C are chloro when A is $N(OR_6)R_2$ or are independently selected from $NHR_3$ and $NR_4R_5$ where $R_1$, $R_2$, $R_3$, $R_4$ and $R_5$ are independently selected from the group consisting of alkyl, cycloalkyl and alkylaryl each of which may be unsubstituted or substituted with one or more substituents selected from the group consisting of hydroxy, OR, NRR, OCOR, OCONRR, NRCOR and NRCONRR where R is selected from the group consisting of hydrogen, alkyl, aryl, alkylaryl, alkoxy and hydroxy or $R_1$ and $R_2$ or $R_4$ and $R_5$ together can form a heteroaryl group and $R_6$ is a member selected from the group consisting of hydrogen, alkyl, alkylaryl and trialkylsilyl; provided that A, B and C cannot be identical, A cannot be piperidino, ethanolamino, diethanolamino, ethylpropylamino, ethylbutylamino or $N(C_{12}H_{25})CH_2CH_2OH$, B and C cannot be diethanolamino or $N(CH\ CH_2CH_2OH)CH_2CH_2CH_3$ and when A is $NR_1R_2$ and $R_1$ and $R_2$ are alkyl, they must be different; and the pharmaceutically acceptable salts thereof.

This invention also relates to pharmaceutical compositions and methods of inhibiting lipoxygenase enzymes and related disorders comprising the administration to a mammal, preferably a human, in need of such treatment of a compound of Formula II:

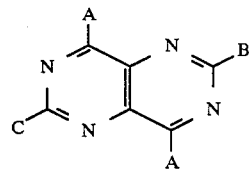

wherein A is selected from $NR_1R_2$ and $N(OR_6)R_2$ and B and C are chloro when A is $N(OR_6)R_2$ or are independently selected from $NHR_3$ and $NR_4R_5$ where $R_1$, R $R_3$, $R_4$ and $R_5$ are independently selected from the group consisting of alkyl, cycloalkyl and alkylaryl each of which may be unsubstituted or substituted with one or more substituents selected from the group consisting of hydroxy, OR, NRR, OCOR, OCONRR, NRCOR and NRCONRR where R is selected from the group consisting of hydrogen, alkyl, aryl, alkylaryl, alkoxy and hydroxy or $R_1$ and $R_2$ or $R_4$ and $R_5$ together can form a heteroaryl group and $R_6$ is a member selected from the group consisting of hydrogen, alkyl, alkylaryl and trialkylsilyl; and the pharmaceutically acceptable salts thereof.

The term "alkyl" as used herein refers to straight and branched chain radicals having 1 to 12 carbon atoms which may be optionally substituted as herein defined. Representative of such radicals are methyl, ethyl, n-propyl, isopropyl, n-butyl, sec-butyl, isobutyl, tert-butyl, and the like.

The term "alkoxy" as used herein refers to straight and branched chain oxygen ether radicals having 1 to 12 carbon atoms which may be optionally substituted. Representative of such radicals are methoxy, ethoxy, isopropoxy, n-butoxy, sec-butoxy, isobutoxy, tert-butoxy, and the like.

The terms "aryl" and "heteroaryl" as used herein refer to mono or polycyclic hydrocarbon groups containing fused or nonfused aromatic ring systems which may contain one or more hetero atoms such as O, N or S in the ring system and which may be optionally substituted as defined herein. Representative of such groups are phenyl, naphthyl, biphenyl, triphenyl, pyridyl, pyrrolyl, pyrimidyl, furyl, thienyl, indolyl, pyrazinyl, isoquinolyl, thiophenyl, benzopyranyl, benzofuryl, benzothiophenyl, imidazolyl, carbazolyl, and the like. Aryl groups may also be linked to alkyl, alkenyl and alkoxy radicals.

The term "cycloalkyl" as used herein refers to saturated and unsaturated cyclic or bicyclic radicals having 3 to 8 carbon atoms which may be optionally substituted as defined above. Representative of such groups are cyclopropyl, cyclobutyl, cyclopentyl, cyclohexyl, norbornyl, 2-chlorocyclohexyl, and the like.

The terms "halo" and "halogen" as used herein refer to radicals derived from the elements fluorine, chlorine, bromine and iodine.

The term "pharmaceutically acceptable salts" refers to the relatively non-toxic, inorganic or organic acid addition salts and alkaline earth metal salts of the compounds of this invention. These salts can be prepared in situ during the final isolation and purification of the compounds, or by separately reacting the free base with a suitable organic or inorganic acid. Representative salts include the hydrochloride, hydrobromide, sulfate, nitrate, bisulfate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactobionate, lauryl sulphate, and the like. Representative alkali or alkaline earth metal sales include sodium, calcium, potassium and magnesium salts, and the like. It will be apparent to those skilled in the art that, depending upon the number of available amino groups for salt formation, the salts of this invention can be per-N-salts.

Certain compounds of this invention may exist in optically active forms. The R and S isomers and mixtures thereof, including racemic mixtures as well as the cis and trans mixtures are contemplated by this invention. Additional asymmetric carbon atoms may be present in a substituent group such as an alkyl group. All such isomers as well as the mixtures thereof are intended to be included in the invention.

The present invention includes one or more of the compounds of Formula I and Formula II formulated into compositions together with one or more non-toxic pharmaceutically acceptable carriers, adjuvants or vehicles which are collectively referred to herein as carriers, for parenteral injection, for oral administration in solid or liquid form, for rectal administration, and the like.

The compositions can be administered to humans and animals either orally, rectally, parenterally (intravenously, intramuscularly or subcutaneously), intracisternally, intravaginally, intraperitoneally, locally (powders, ointments or drops), or as a buccal or nasal spray.

Compositions suitable for parenteral injection may comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

If desired, and for more effective distribution, the compounds can be incorporated into slow release or targeted delivery systems such as polymer matrices, liposomes, and microspheres. They may be sterilized, for example, by filtration through a bacteria-retaining filter, or by incorporating sterilizing agents in the form of sterile solid compositions which can be dissolved in sterile water, or some other sterile injectable medium immediately before use.

Solid dosage forms for oral administration include capsules, tablets, pills, powders and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alignates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules using such excipients as lactose or milk sugar as well as high molecular weight polyethylene glycols, and the like.

Solid dosage forms such as tablets, dragees, capsules, pills and granules can be prepared with coatings and shells, such as enteric coatings and others well known in this art. They may contain opacifying agents, and can also be of such composition that they release the active compound or compounds in a certain part of the intestinal tract in a delayed manner. Examples of embedding compositions which can be used are polymeric substances and waxes.

The active compounds can also be in micro-encapsulated form, if appropriate, with one or more of the abovementioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame oil, glycerol, tetrahydrofurfuryl alcohol, polyethylene glycols and fatty acid esters of sorbitan or mixtures of these substances, and the like.

Besides such inert diluents, the composition can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of this invention with suitable non-irritating excipients or carriers such as cocoa butter, polyethylene glycol or a suppository wax, which are solid at ordinary temperatures but liquid at body temperature and therefore, melt in the rectum or vaginal cavity and release the active component.

Dosage forms for topical administration of a compound of this invention include powders, sprays and inhalants. The active component is admixed under sterile conditions with a pharmaceutically acceptable carrier and any needed preservatives, buffers or propellants as may be required. Opthalmic formulations, eye ointments, powders and solutions are also contemplated as being within the scope of this invention.

The present compounds can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the lipoxygenase inhibiting compounds of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Actual dosage levels of active ingredient in the compositions of the invention may be varied so as to obtain an amount of active ingredient that is effective to obtain a desired therapeutic response for a particular composition and method of administration. The selected dosage level therefore depends upon the desired therapeutic effect, on the route of administration, on the desired duration of treatment and other factors.

Total daily dose of the compounds of this invention administered to a host in single or divided doses may be in amounts, for example, of from about 0.001 to about 100 mg/kg body weight daily and preferably 0.01 to 10 mg/kg/day. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

Pyrimido-pyrimidine compounds of Formula I and Formula II can be prepared by the reaction sequence outlined in Scheme I. The precursor 2,4,6,8-tetrachloropyrimidopyrimidine (1) is reacted with two or more equivalents of an amine derivative A to provide the intermediate 2. Heating intermediate 2 with an amine derivative B will displace chlorine to provide intermediate 3 and at a slower reaction rate an amine derivative C will displace the chlorine in 3 to provide the product 4 where A, B and C are as defined herein. For examples where C is hydrogen, these compounds can be prepared by hydrogenolysis of the chloride intermediate 3.

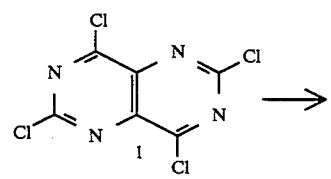

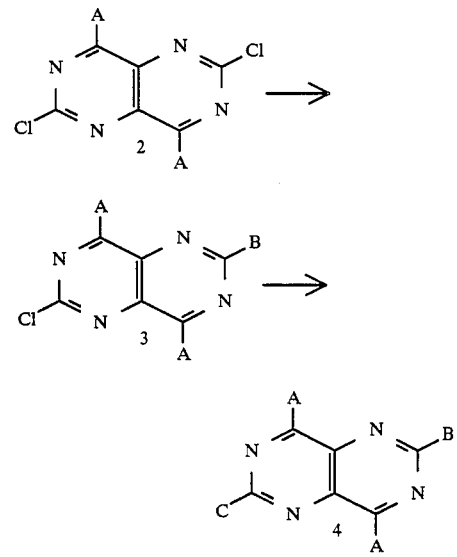

Example 1.
2,6-bis-2-(Methylamino)ethanol-4,8-bis-N-piperidinopyrimido[5,4-d]pyrimidine (a). To a solution of 2,4,6,8-tetrachloropyrimidopyrimidine (1 g, 4 mmol) in dioxane (20 mL) was added piperidine (1.3 g, 15.2 mmol) and the mixture was stirred for 5 minutes at 23° C., diluted with water (100 mL) and the precipitate was collected by filtration. Recrystallization from methanol benzene (1:1) gave 2,6-dichloro-4,8-bis-N-piperidino[5,4-d]pyrimidine; mp 247°–248° C.

(b). 2,6-Dichloro-4,8-bis-N-piperidinopyrimido[5,4-d]pyrimidine (0.5g, 1.36 mmol) and 2-(methylamino)ethanol (1.0 mL, 11.7 mmol) were heated at 200°–220° C. for 30 minutes under nitrogen. The residue was chromatographed (silica gel, 2% methanol in dichloromethane) to afford 2,6-bis-2-(methylamino)ethanol-4,8-bis-N-piperidinopyrimido[5,4d]pyrimidine (1.53g, 84% yield); mp 132°–134° C.; 1H NMR (300 MHz, DMSO-$d_6$) 1.55–1.7 (12 H, m), 3.07 (6 H, s), 3.56 (8 H, s), 4.07 (8 H, br s), 4.61 (2 H, t, J =7.5 Hz); MS M+ =444.

Analysis Calc'd. for $C_{22}H_{36}N_8O_2$: C, 59.44; H, 8.16; N, 25.20.
Found: C., 58.96; H, 8.09; N, 24.91.

Example 2.
2,6-bis-Aminoethanol-4,8-bis-N-piperidinopyrimido[5,4-d]pyrimidine

The title compound was prepared according to the method of Scheme 1 as described for Example 1, except ethanolamine was used instead of 2-methylaminoethanol; mp 158°–160° C; 1H NMR (300 MHz, DMSO-$d_6$) 1.55–1.7 (12 H, m), 3.2–3.3 (4 H, m), 3.47–3.55 (4 H, m), 4.05 (8 H, br s), 4.61 (2 H, t, J =6Hz), 6.02 (2 H, t, J=6Hz); MS, M+ =416.

Example 3.
2,6-bis-2-(Methylamino)ethanol-4,8-bis-N-perhydroazepinepyrimido-[5,4-d]pyrimidine The title compound was prepared according to the method of Scheme 1 as described for Example 1, except perhydroazepine (hexamethyleneimine) was used instead of 2-methylaminoethanol; 1H NMR (300 MHz, DMSO-d$_6$, at 95° C.) 1.55 (8 H, m), 1.8 (8 H, m), 3.06 (6 H, m), 4.16 (10 H, m); MS, M+ =472.

Example 4.
2,6-bis-2-(Methylamino)ethanol-4,8-bis-N-perhydroazocinepyrimido[5,4-d]pyrimidine The title compound was prepared according to the method of Scheme 1 as described for Example 1, except perhydroazocine (heptamethyleneimine) was used instead of 2-methylaminoethanol; 1H NMR (300 MHz, DMSO-d$_6$) 1.4–1.6 (12 H, m) 1.8 (8 H, m), 3.06 (6 H, s), 3.6 (8 H, m), 4.15 (8 H, br t), 4.25 (2 H, m); MS, M+ =500.

Example 5.
2,6-Dichloro-4,8-bis-N-methylhydroxylaminopyrimido[5,4-d]pyrimidine (a) To a solution of 2,4,6,8-tetrachloropyrimidopyrimidine (1 g, 4 mmol) in dioxane (20 mL) was added N-methyl-O-t-butyldimethylhydroxylamine (2.6 g, 16 mmol) and the mixture was stirred for 1.5 hours at 23° C., diluted with cold water (160 mL), and the precipitate was collected by filtration and washed with water. After drying in vacuo the desired intermediate was obtained (1.86 g, 89%); mp 181°–183° C.

(b) To a solution of the O-protected pyrimidopyrimidine intermediate (0.78 g, 1.5 mmol), from the previous step cooled to 0° C. in tetrahydrofuran (5 mL) was added tetra n-butylammonium fluoride. The mixture was stirred for 10 minutes then cold aqueous ethanol was added to give a precipitate which was collected by filtration and washed with cold ethanol to yield the desired product (0.68 g, 78%); 1H NMR (300 MHz, DMSO-d$_6$ 3.8 (6 H, s), 11.3 (2H, s); MS, M+ =290.

Analysis Calc'd. for C$_8$H$_8$Cl$_2$N$_6$O$_2$: C, 33.01; H, 2.77; N, 28.87
Found: C, 33.05; H, 2.90; N, 28.25.

Other representative compounds of Formula I as shown in Table 1 can be prepared according to the method of Scheme 1 in an analogous manner as for Example 1 by substituting the appropriate amine or hydroxylamine derivative to provide the requisite groups A, B, and C.

TABLE 1

| A | B = C |
|---|---|
| perhydroazepino | —N(CH$_2$CH$_3$)CH$_2$CH$_2$OH |
| perhydroazepino | —N(CH$_2$(CH$_3$)$_2$CH$_2$CH$_2$OH |
| perhydroazepino | —NHCH$_2$CH$_2$OH |
| perhydroazepino | morpholino |
| perhydroazepino | 2-(cyclohexylamino)ethanol |
| perhydroazepino | —N(CH$_3$)CH$_2$CH$_2$OCONH$_2$ |
| perhydroazepino | —N(CH$_3$)CH$_2$CH$_2$NHCONH$_2$ |
| perhydroazepino | —N(CH$_3$)CH$_2$CH$_2$N(OH)CONH$_2$ |
| perhydroazepino | —N(CH$_3$)CH$_2$CH$_2$NHCOCH$_3$ |
| perhydroazepino | —N(CH$_3$)CH$_2$CH$_2$N(OH)COCH$_3$ |
| perhydroazocino | —N(CH$_2$CH$_3$)CH$_2$CH$_2$OH |
| perhydroazocino | —N(CH$_2$CH$_3$)CH$_2$CH$_2$OH |
| perhydroazocino | —N(CH$_2$(CH$_3$)$_2$CH$_2$CH$_2$OH |
| perhydroazocino | —NHCH$_2$CH$_2$OH |
| perhydroazocino | morpholino |
| perhydroazocino | 2-(cyclohexylamino)ethanol |
| perhydroazocino | —N(CH$_3$)CH$_2$CH$_2$OCONH$_2$ |
| perhydroazocino | —N(CH$_3$)CH$_2$CH$_2$NHCONH$_2$ |
| perhydroazocino | —N(CH$_3$)CH$_2$CH$_2$N(OH)CONH$_2$ |
| perhydroazocino | —N(CH$_3$)CH$_2$CH$_2$NHCOCH$_3$ |
| perhydroazocino | —N(CH$_3$)CH$_2$CH$_2$N(OH)COCH$_3$ |
| dibutylamino | —N(CH$_3$)CH$_2$CH$_2$OH |
| —N(CH$_3$)CH$_2$CH$_2$OH | morpholino |

Inhibition of 5-Lipoxygenase

Inhibition of 5-lipoxygenase activity was determined using the 20,000x g supernatant from homogenized RBL-1 cells in a similar manner as that described by Dyer and coworkers (Dyer, R.D.; Haviv, F,; Hanel, A. M.; Bornemier, D. A.; Carter, G. W. Fed. Proc., Fed. Am. Soc. Exp. Biol. 1984, 43, 1462A). Inhibitory potencies for representative examples of this invention are listed in Table 2. IC$_{50}$ values (concentration of compound producing 50% enzyme inhibition) were calculated by linear regression analysis of percentage inhibition versus log inhibitor concentration plots.

TABLE 2

In vitro 5-lipoxygenase inhibitory potency of representative compounds of this invention.

| Example | Inhibition (IC$_{50}$) |
|---|---|
| 1 | 0.34 μM |
| 2 | 2.9 μM |
| 3 | 0.30 μM |
| 4 | 0.92 μM |
| 5 | 96% at 3 μM |

We claim:

1. A composition for the inhibition of lipoxygenase enzymes comprising a pharmaceutically acceptable carrier and a compound of the formula:

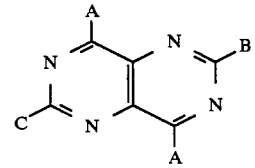

wherein A is perhydroazocinyl; and B and C are independently selected from NHR$_3$ and NR$_4$R$_5$ where R$_3$, R$_4$ and R$_5$ are independently selected from the group consisting of alkyl from one to twelve carbon atoms, cycloalkyl of from three to either carbon atoms and alkylaryl in which the alkyl portion is as previously defined and the aryl portion is selected from phenyl, naphthyl, biphenyl, and terphenyl, each of said alkyl cycloalkyl, and alkylaryl groups being unsubstituted or substituted with one or more substituents selected from the group consisting of hydroxy, alkoxy of from one to twelve carbon atoms, NRR, OCOR, OCONRR, NRCOR and NRCONRR where R is selected from the group consisting of hydrogen, alkyl as previously defined, aryl as previously defined, alkylaryl as previously defined, alkoxy as previously defined and hydroxy, or R$_4$ and R$_5$ together can form a heteroaryl group selected from the group consisting of pyridyl, pyrrolyl, pyrimidyl, indolyl, pyrazinyl, isoquinolyl, imidazolyl and carbazolyl; and the pharmaceutically acceptable salts thereof.

2. A method for the inhibition of lipoxygenase enzymes comprising administration to a mammal in need of such treatment of an effective amount of a compound of the formula:

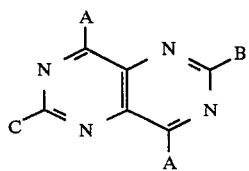

wherein A is perhydroazocinyl; and B and C are independently selected from NHR$_3$ and NR$_4$R$_5$ where R$_3$, R$_4$ and R$_5$ are independently selected from the group consisting of alkyl from one to twelve carbon atoms, cycloalkyl of from three to eight carbon atoms and alkylaryl in which the alkyl portion is as previously defined and the aryl portion is selected from phenyl, naphthyl, biphenyl, and terphenyl, each of said alkyl, cycloalkyl, and alkylaryl groups being unsubstituted or substituted with one or more substituents selected from the group consisting of hydroxy, alkoxy of from one to twelve carbon atoms, NRR, OCOR, OCONRR, NRCOR and NRCONRR where R is selected from the group consisting of hydrogen, alkyl as previously defined, aryl as previously define, alkylaryl as previously defined, alkoxy as previously defined and hydroxy, or R$_4$ and R$_5$ together can form a heteroaryl group selected from the group consisting of pyridyl, pyrrolyl, pyrimidyl, indolyl, pyrazinyl, isoquinolyl, imidazolyl and carbazolyl; and the pharmaceutically acceptable salts thereof.

3. The compound having the name 2,6-bis(2-(methylamino)ethanol)-4,8-bis(N-perhydroazocinyl)-pyrimido[5,4-d]pyrimidine or a pharmaceutically acceptable salt thereof.

* * * * *

UNITED STATES PATENT AND TRADEMARK OFFICE
CERTIFICATE OF CORRECTION

PATENT NO. : 4,963,541
DATED : OCTOBER 16, 1990
INVENTOR(S) : DEE W. BROOKS; ANWER BASHA

It is certified that error appears in the above-identified patent and that said Letters Patent is hereby corrected as shown below:

COLUMN 3, LINE 59: REPLACE "$N(CH\ CH_2CH_2OH)CH_2CH_2CH_3$" WITH
$--N(CH_2CH_2OH)CH_2CH_2OCH_3--$

COLUMN 4, LINE 10: REPLACE "$N(OR_6)R_2 and$" with $--N(OR_6)R_2;\ and--$

COLUMN 4, LINE 12: REPLACE "$R_1,\ R\ R_3,$" with $--R_1,\ R_2,\ R_3,--$

COLUMN 8, LINE 44: REPLACE "[5,4d]" with --[5,4-d]--

Signed and Sealed this

Twenty-first Day of April, 1992

Attest:

HARRY F. MANBECK, JR.

Attesting Officer     Commissioner of Patents and Trademarks